(12) United States Patent
Hasson (10) Patent No.: US 9,777,318 B2
(45) Date of Patent: Oct. 3, 2017

(54) SYSTEMS AND METHODS FOR MONITORING THE AMPLIFICATION OF DNA

(71) Applicant: Canon U.S. Life Sciences, Inc., Rockville, MD (US)

(72) Inventor: Kenton C. Hasson, Gaithersburg, MD (US)

(73) Assignee: Canon U.S. Life Sciences, Inc., Rockville, MD (US)

( * ) Notice: Subject to any disclaimer, the term of this patent is extended or adjusted under 35 U.S.C. 154(b) by 0 days.

(21) Appl. No.: 14/697,036

(22) Filed: Apr. 27, 2015

(65) Prior Publication Data

US 2015/0225779 A1 Aug. 13, 2015

Related U.S. Application Data

(62) Division of application No. 12/144,223, filed on Jun. 23, 2008, now Pat. No. 9,017,946.

(51) Int. Cl.
*C12Q 1/68* (2006.01)

(52) U.S. Cl.
CPC .................................. *C12Q 1/686* (2013.01)

(58) Field of Classification Search
CPC ...................................................... C12C 1/68
See application file for complete search history.

(56) References Cited

U.S. PATENT DOCUMENTS

| | | | |
|---|---|---|---|
| 5,631,734 A | 5/1997 | Stern et al. | |
| 5,814,524 A | 9/1998 | Walt et al. | |
| 5,880,071 A | 3/1999 | Parce et al. | |
| 5,928,907 A | 7/1999 | Woudenberg et al. | |
| 6,450,203 B1 | 9/2002 | Backhouse et al. | |
| 6,561,208 B1 | 5/2003 | O'Connor et al. | |
| 6,569,631 B1 | 5/2003 | Pantoliano et al. | |
| 6,589,791 B1 | 7/2003 | LaBudde et al. | |
| 6,619,311 B2 | 9/2003 | O'Connor et al. | |
| 6,662,818 B2 | 12/2003 | Paul et al. | |
| 6,779,559 B2 | 8/2004 | Parce et al. | |
| 6,802,342 B2 | 10/2004 | Fernandes et al. | |
| 6,877,528 B2 | 4/2005 | Gilbert et al. | |
| 6,953,058 B2 | 10/2005 | Fernandes et al. | |
| 7,244,961 B2 | 7/2007 | Jovanovich et al. | |
| 2005/0069257 A1 | 3/2005 | Bhagavatula et al. | |
| 2005/0075683 A1 | 4/2005 | Miesel et al. | |
| 2006/0006067 A1 | 1/2006 | Unger | |
| 2006/0223172 A1 | 10/2006 | Bedingham et al. | |
| 2008/0003588 A1 | 1/2008 | Hasson et al. | |
| 2008/0182301 A1 | 7/2008 | Handique et al. | |

FOREIGN PATENT DOCUMENTS

WO 00/68671 A2 11/2000
WO 2004/083443 A1 9/2004

*Primary Examiner* — Cynthia B Wilder
(74) *Attorney, Agent, or Firm* — Rothwell, Figg, Ernst & Manbeck, P.C.

(57) ABSTRACT

A system and method for amplifying and detecting nucleic acids are disclosed. In one embodiment, the system includes: a microfluidic device comprising a channel for receiving a sample of solution containing real-time PCR reagents; a temperature control system configured to cycle the temperature of the sample; an excitation source for illuminating the sample; a fiber optic probe comprising (i) an optical fiber having a distal end and a proximal end and (ii) a probe head connected to the distal end of the optical fiber and positioned between the distal end of the optical fiber and the channel; and a detector configured to detect emissions exiting the proximal end of the optical fiber.

7 Claims, 10 Drawing Sheets

SYSTEMS AND METHODS FOR MONITORING THE AMPLIFICATION OF DNA

CROSS-REFERENCE TO RELATED APPLICATION

This application is a divisional of U.S. patent application Ser. No. 12/144,223, filed on Jun. 23, 2008, the disclosure of which is hereby incorporated by reference in its entirety.

BACKGROUND

Field of the Invention

This invention pertains to systems and methods for amplifying and detecting nucleic acids. In one embodiment, it pertains to methods for monitoring a polymerase chain reaction (PCR) in a microfluidic system.

Discussion of the Related Art

The detection of nucleic acids is central to medicine, forensic science, industrial processing, crop and animal breeding, and many other fields. The ability to detect disease conditions (e.g., cancer), infectious organisms (e.g., HIV), genetic lineage, genetic markers, and the like, is ubiquitous technology for disease diagnosis and prognosis, marker assisted selection, correct identification of crime scene features, the ability to propagate industrial organisms and many other techniques. Determination of the integrity of a nucleic acid of interest can be relevant to the pathology of an infection or cancer. One of the most powerful and basic technologies to detect small quantities of nucleic acids is to replicate some or all of a nucleic acid sequence many times, and then analyze the amplification products. PCR is perhaps the most well-known of a number of different amplification techniques.

PCR is a powerful technique for amplifying short sections of DNA. With PCR, one can quickly produce millions of copies of DNA starting from a single template DNA molecule. PCR includes a three phase temperature cycle of denaturation of DNA into single strands, annealing of primers to the denatured strands, and extension of the primers by a thermostable DNA polymerase enzyme. This cycle is repeated so that there are enough copies to be detected and analyzed. In principle, each cycle of PCR could double the number of copies. In practice, the multiplication achieved after each cycle is always less than 2. Furthermore, as PCR cycling continues, the buildup of amplified DNA products eventually ceases as the concentrations of required reactants diminish. For general details concerning PCR, see Sambrook and Russell, *Molecular Cloning—A Laboratory Manual* (3rd Ed.), Vols. 1-3, Cold Spring Harbor Laboratory, Cold Spring Harbor, N.Y. (2000); *Current Protocols in Molecular Biology*, F. M. Ausubel et al., eds., Current Protocols, a joint venture between Greene Publishing Associates, Inc. and John Wiley & Sons, Inc., (supplemented through 2005) and *PCR Protocols A Guide to Methods and Applications*, M. A. Innis et al., eds., Academic Press Inc. San Diego, Calif. (1990).

Real-time PCR refers to a growing set of techniques in which one measures the buildup of amplified DNA products as the reaction progresses, typically once per PCR cycle. Monitoring the accumulation of products over time allows one to determine the efficiency of the reaction, as well as to estimate the initial concentration of DNA template molecules. For general details concerning real-time PCR see *Real-Time PCR: An Essential Guide*, K. Edwards et al., eds., Horizon Bioscience, Norwich, U.K. (2004).

Several different real-time detection chemistries now exist to indicate the presence of amplified DNA. Most of these depend upon fluorescence indicators that change properties as a result of the PCR process. Among these detection chemistries are DNA binding dyes (such as SYBR® Green) that increase fluorescence efficiency upon binding to double stranded DNA. Other real-time detection chemistries utilize Foerster resonance energy transfer (FRET), a phenomenon by which the fluorescence efficiency of a dye is strongly dependent on its proximity to another light absorbing moiety or quencher. These dyes and quenchers are typically attached to a DNA sequence-specific probe or primer. Among the FRET-based detection chemistries are hydrolysis probes and conformation probes. Hydrolysis probes (such as the TaqMan® probe) use the polymerase enzyme to cleave a reporter dye molecule from a quencher dye molecule attached to an oligonucleotide probe. Conformation probes (such as molecular beacons) utilize a dye attached to an oligonucleotide, whose fluorescence emission changes upon the conformational change of the oligonucleotide hybridizing to the target DNA.

A number of commercial instruments exist that perform real-time PCR. Examples of available instruments include the Applied Biosystems PRISM 7500, the Bio-Rad iCylcer, and the Roche Diagnostics LightCycler 2.0. The sample containers for these instruments are closed tubes which typically require at least a 10 µl volume of sample solution. If the lowest concentrations of template DNA detectable by a particular assay were on the order of one molecule per microliter, the detection limit for available instruments would be on the order of tens of targets per sample tube.

More recently, a number of high throughput approaches to performing PCR and other amplification reactions have been developed, e.g., involving amplification reactions in microfluidic devices, as well as methods for detecting and analyzing amplified nucleic acids in or on the devices. Thermal cycling of the sample for amplification is usually accomplished in one of two methods. In the first method, the sample solution is loaded into the device and the temperature is cycled in time, much like a conventional PCR instrument. In the second method, the sample solution is pumped continuously through spatially varying temperature zones.

U.S. patent application Ser. No. 11/505,358, entitled, "Real-time PCR in micro-channels," which is assigned to the assignee of this application and which is incorporated herein by this reference in its entirety, describes, among other things, a novel method to acquire real-time PCR data in a microfluidic system. One of the steps in that method is to capture an image of a fluorescent signal along the length of at least one microfluidic channel.

Figure 1:
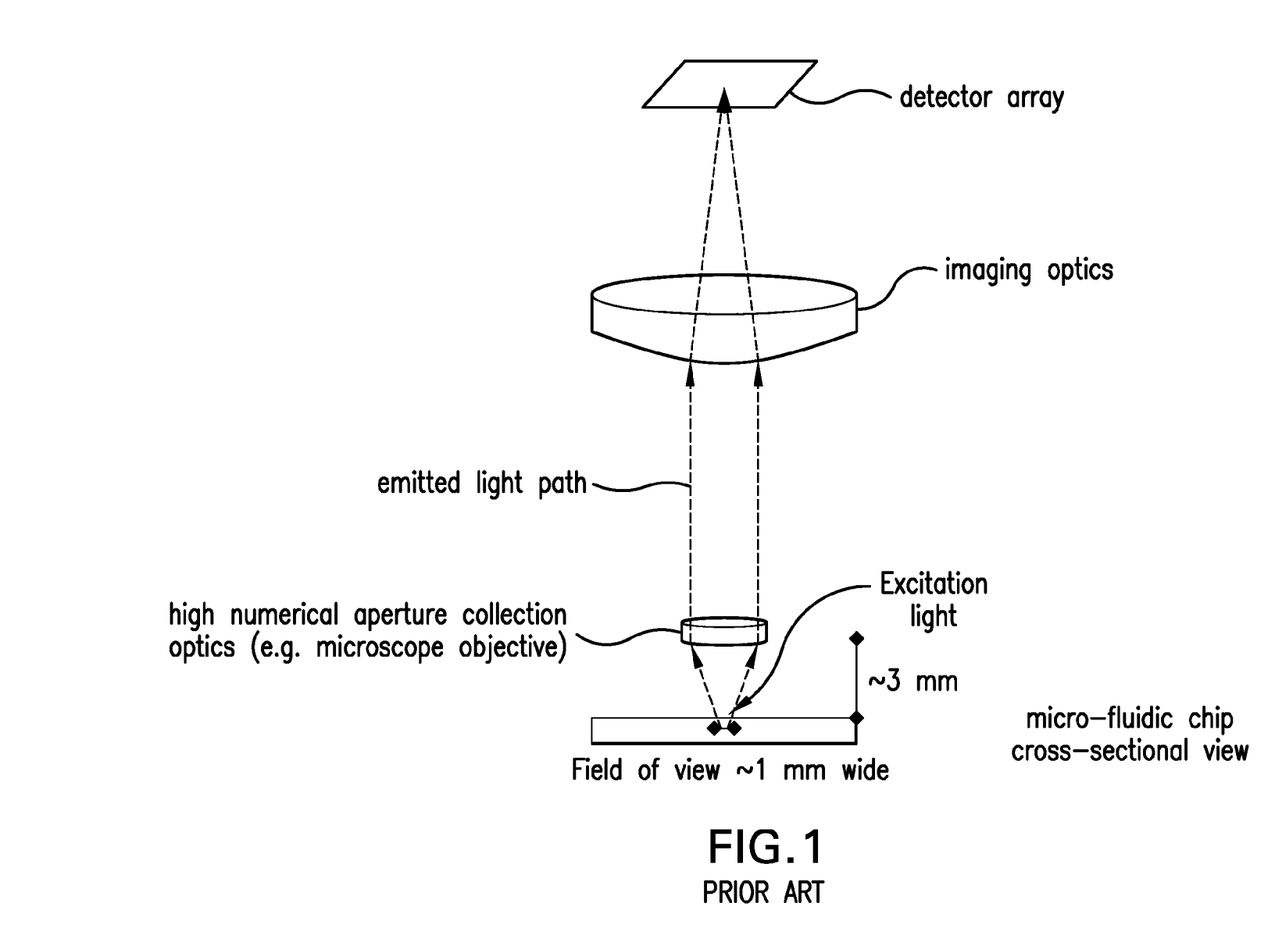
FIG. 1 depicts a prior art apparatus to capture an image of a fluorescent signal.

A conventional apparatus to capture an image of a fluorescent signal is illustrated in FIG. 1. As illustrated in FIG. 1, the light emitted from the material under study is collected by a high numerical aperture objective and the light is re-imaged onto a two-dimensional detector array.

A reason for using a high numerical aperture objective to collect luminescence is that the solid angle subtended is higher, and therefore the photon collection efficiency is higher, than that achieved using a low numerical aperture objective. In certain cases, collection efficiency may be an important parameter because, in certain cases, emitted light flux is often so low that signal levels at the detector are weak. Therefore, at least in certain cases, it is desirable to maximize collection efficiency.

The drawback of using a high numerical aperture microscope objective is that the imaged area is small. The effective field of view of a conventional fluorescence microscope imaging system might have a linear dimension of 1 mm or smaller. This becomes a problem when the region of interest on a microfluidic chip is larger (e.g., if the length and width are in the range of 10-100 mm).

One strategy to address the problem of imaging a large region of interest with high collection efficiency is to use an optical system with large diameter optics. This strategy has a benefit that most or all of the region of interest may be imaged simultaneously. An example of this approach is illustrated in U.S. Patent Application 2006/0006067, entitled, "Optical Lens System and Method for Microfluidic Devices," which describes a multi-element lens system.

Another strategy would be to translate the sample holder with respect to the optical system or vice versa (e.g. in a raster pattern) to collect pixel data in series. An example of this approach is described in U.S. Pat. No. 5,631,734, entitled, "Method and Apparatus for Detection of Fluorescently Labeled Materials." This patent describes a system for collecting fluorescence data from a substrate, for example a DNA microarray, in which the substrate is held by an x-y-z translation stage and translated in front of a microscope objective.

PCT publication WO 2005/075683 A1, entitled, "High Throughput Device for Performing Continuous-Flow Reactions," describes a continuous-flow PCR device that uses a fused silica capillary wrapped into a helix around three temperature-controlled blocks. This publication shows a microscope objective lens being scanned transverse to the windings. Although the description is short on detail, presumably an entire optical imaging system, including lenses, beam-splitters, filters, and detectors, would have to be scanned along as well.

U.S. Pat. No. 5,928,907, entitled, "System for Real Time Detection of Nucleic Acid Amplification Products," describes a system for real-time PCR monitoring that uses a fiber optic and a lens to capture fluorescence from a closed, Eppendorf-style sample tube. The sample tube volume was 200 ul, and the fiber optic and 8 mm diameter collection lens were fixed with respect to the tube, looking down through the top of the tube and the airspace over the sample solution.

U.S. Patent Application 2005/0069257 A1, "Fiber Lens with Multimode Pigtail" gives an example of a miniature lens system that is permanently affixed to the end of an optical fiber. Further examples of miniature fiber coupling systems can be found in product literature by Corning Inc. for lensed fibers, tapered fibers, and gradient index fibers and lenses. These devices are used typically in telecommunication equipment, for example, for coupling light from a semiconductor diode laser into an optical fiber, or for coupling light from one fiber into another fiber.

SUMMARY OF THE INVENTION

The present invention provides, among other things, improved systems and methods for capturing an image of a fluorescent signal. In addition, the present invention may be useful in a variety of additional applications.

A system according to an embodiment of the invention includes: a microfluidic device comprising a channel for receiving a sample of solution containing real-time PCR reagents; a temperature control system configured to cycle the temperature of the sample; and an imaging system for detecting emissions from the sample, wherein the imaging system comprises: an excitation source for illuminating the sample, a fiber optic probe comprising (i) an optical fiber having a distal end and a proximal end and (ii) a probe head connected to the distal end of the optical fiber and positioned between the distal end of the optical fiber and the channel, and a detector configured to detect emissions exiting the proximal end of the optical fiber.

The probe head had may be positioned directly above the channel and may be positioned no more than about 10 millimeters from the top of the channel. The system may also include: a positioning system configured to scan the fiber optic probe over at least a portion of the channel and a pump for causing the sample to flow through the channel. In such embodiments, the positioning system may be configured to scan the fiber optic probe over the portion of the channel at a speed that is greater than the speed at which the sample is expected to flow through the channel.

In some embodiments, the imaging system may also include a second fiber optic probe comprising (i) an optical fiber having a distal end and a proximal end and (ii) a probe head connected to the distal end of the optical fiber and positioned between the distal end of the optical fiber and the channel. In such a system, the first fiber optic probe may have a first field of view and the second fiber optic probe may have a second field of view, wherein a first portion of the channel is within the first field of view but not the second field of view and a second portion of the channel is within the second field of view but not the first field of view.

With respect to the probe head, in some embodiments, the probe head includes a ball lens, a gradient index lens, a liquid lens, or a high index liquid. The probe head may have a diameter between about 0.1 millimeters (mm) and 5 mm, but more preferably between about 0.5 mm and 2 mm. Additionally, in some embodiments the distance between the probe head and the channel is less than 10 mm (e.g., about 1 mm in some embodiments). With respect to the optical fiber, in some embodiments, the optical fiber includes: a multimode fiber, a liquid filled fiber, a photonic crystal fiber.

In some embodiments, the excitation source is optically connected to the optical fiber such that when the excitation source emits excitation light, the excitation light enters the optical fiber and then exits the optical fiber through the distal end of the optical fiber.

In some embodiments, the microfluidic device further includes a second channel for receiving a second sample of solution containing real-time PCR reagents, and the imaging system further comprises a second fiber optic probe comprising (i) an optical fiber having a distal end and a proximal end and (ii) a probe head connected to the distal end of the optical fiber and positioned between the distal end of the optical fiber and the second channel, and a second detector configured to detect emissions exiting the proximal end of the optical fiber of the second fiber optic probe. In such embodiments, the system may include a positioning system configured to scan the first fiber optic probe over at least a portion of the first channel and simultaneously scan the second fiber optic probe over at least a portion of the second channel.

In some embodiments, one or more filters may be positioned between the proximal end of the optical fiber and the detector. The one or more filters may include a tunable wavelength filter.

A system according to another embodiment includes: a sample container for containing a sample of a solution containing real-time PCR reagents; a temperature control system configured to cycle the temperature of the sample; an excitation source for illuminating the sample; a fiber optic probe comprising: a bundle of optical fibers including a central optical fiber surrounded by a plurality of outer optical fibers, and a probe head connected to a distal end of the central optical fiber and positioned between the distal end of the central optical fiber and the sample container, and a detector configured to detect emissions exiting the proximal end of the central optical fiber, wherein the excitation source is optically connected to each of the plurality of outer optical fibers such that when the excitation source emits excitation light, the excitation light enters the outer optical fibers and then exits the outer optical fibers through a distal end of the optical fibers. The sample container may be in the form of a channel.

In some embodiments, the excitation source comprises at least two light emitting devices, wherein each of the at least two light emitting devices is optically connected to at least one of the outer optical fibers.

A method according to some embodiments of the invention includes: (a) moving a sample of test solution containing real-time PCR reagents through a channel; (b) while the sample is moving through a section of the channel (i) cycling the temperature of the sample in order to achieve PCR, (ii) illuminating the sample with excitation light, and (iii) using a fiber optic probe to capture fluorescent light emitted from the sample; and (c) measuring the intensity of the fluorescent light.

In some embodiments, the fiber optic probe includes: (i) an optical fiber having a proximal end and a distal end and (ii) a probe head connected to and positioned adjacent to the distal end of the optical fiber, the probe head having a field of view and being positioned such that at least a portion of the section of the channel is within the field of view. The probe head may be positioned directly above the channel and may be positioned no more than about 10 millimeters from the top of the channel.

In some embodiments, the method further includes moving the fiber optic probe along at least the section of the channel while using the fiber optic probe to capture the fluorescent light. The speed at which the fiber optic probe is moved along the section of the channel may be greater than the speed at which the sample moves through the channel (in some embodiments it may be at least 10 times greater).

In some embodiments, the method further includes using a second fiber optic probe to capture fluorescent light emitted from the sample while the sample is moving through the section of the channel. In some embodiments, all the while the sample is moving through the section of the channel, the first fiber optic probe and the second fiber optic probe are fixed in position relative to the channel.

The above and other embodiments of the present invention are described below with reference to the accompanying drawings.

BRIEF DESCRIPTION OF THE DRAWINGS

The accompanying drawings, which are incorporated herein and form part of the specification, illustrate various embodiments of the present invention. In the drawings, like reference numbers indicate identical or functionally similar elements.

DETAILED DESCRIPTION OF PREFERRED EMBODIMENTS

As used herein, the words "a" and "an" mean "one or more."

Aspects of the present invention provide a system for detecting fluorescence emitted from a microfluidic device using at least one fiber optic probe.

Figure 2:
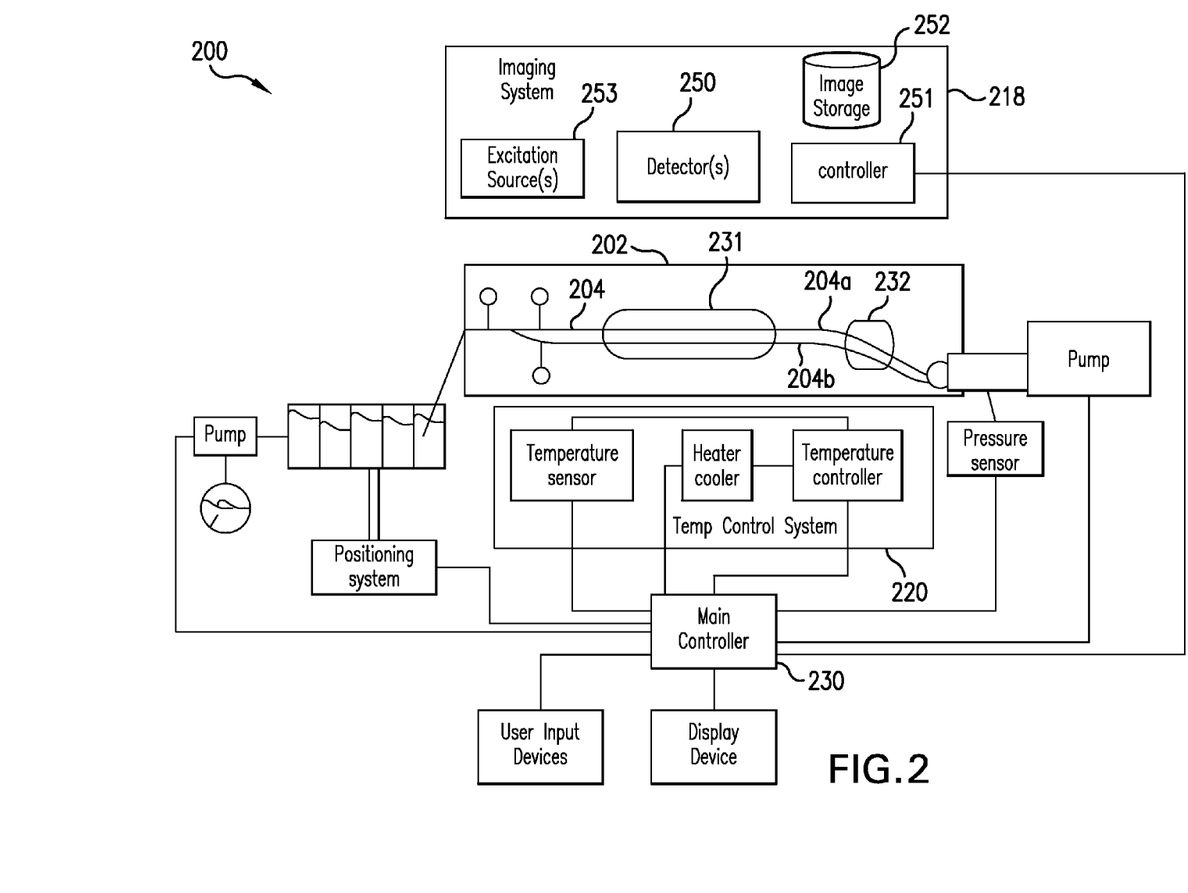
FIG. 2 is a block diagram illustrating a system according to some embodiments of the invention.

FIG. 2 illustrates a functional block diagram of a system 200 according to some embodiments of the invention. As illustrated in FIG. 2, system 200 may include a microfluidic device 202. Microfluidic device 202 may be a microfluidic chip. Microfluidic device 202 may include one or more microfluidic channels 204. In the example shown, device 202 includes two microfluidic channels, channel 204a and channel 204b. Although only two channels are shown in the exemplary embodiment, it is contemplated that device 202 may have fewer than two or more than two channels. For example, in some embodiments, device 202 includes eight channels 204.

Device 202 may include two DNA processing zones, a DNA amplification zone 231 (a.k.a., PCR zone 231) and a DNA melting zone 232. A DNA sample traveling through the PCR zone 231 may undergo PCR, and a DNA sample passing through melt zone 232 may undergo high resolution thermal melting. As illustrated in FIG. 2, PCR zone 231 includes a first portion of channels 204 and melt zone 232 includes a second portion of channels 204, which is down stream from the first portion.

In order to achieve PCR for a DNA sample flowing through the PCR zone 231, the temperature of the sample must be cycled, as is well known in the art. Accordingly, in some embodiments, system 200 includes a temperature control system 220. The temperature control system 220 may include a temperature sensor, a heater/cooler, and a temperature controller. In some embodiments, a temperature control system 220 is interfaced with main controller 230 so that main controller 230 can control the temperature of the samples flowing through the PCR zone and the melting zone.

To monitor the PCR process and the thermal melting process that occur in PCR zone 231 and melt zone 232, respectively, system 200 may include an imaging system 218. Imaging system 218 may include an excitation source 253, a detector 250, a controller 251, and an image storage unit 252.

Further features of system 200 are described in U.S. patent application Ser. No. 11/770,869, which is incorporated herein by this reference in its entirety.

Figure 3:
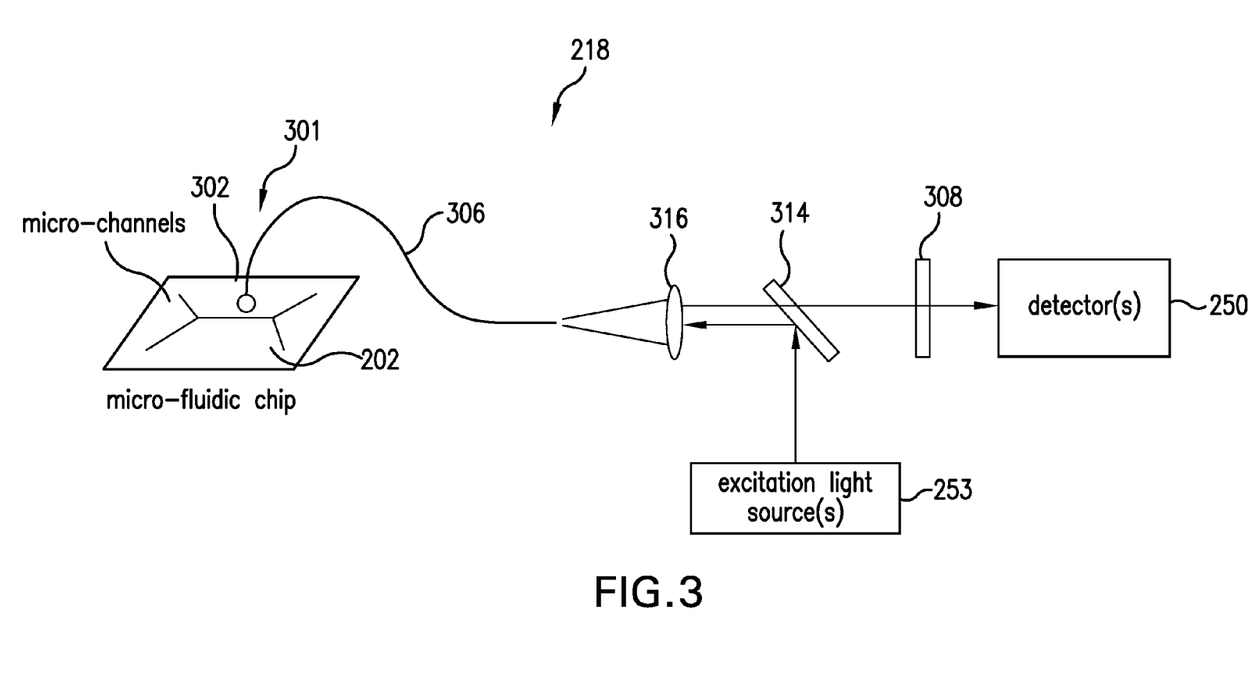
FIG. 3 is a diagram of a close-up side view of a possible probe head assembly.

Referring now to FIG. 3, an embodiment of imaging system 218 is illustrated. As shown in FIG. 3, imaging system 218 may include a fiber optic probe 301 that includes a probe head 302 connected to an optical fiber 306, which directs fluorescent light to a light sensor or detector array 250. Suitable detectors would include, but not be limited to: photomultiplier tubes; micro-channel plate detectors; photoconductors; photodiodes (include avalanche photodiodes); and detector areas including CCD and CMOS detector arrays. Fixed and/or tunable wavelength filters 308 discriminate against unwanted wavelengths such as scattered excitation light. In addition, the fluorescence may be dispersed spectrally onto a plurality of detectors by using devices such as diffraction gratings, prisms, or multilayer dielectric wavelength filters.

Excitation light may be directed onto the microfluidic device 202 in the same location where the probe head 302 is set to collect emitted light. The excitation light may comprise light of multiple wavelengths and may be generated by a variety of light sources. In addition, excitation light may be directed onto the microfluidic device 202 in a variety of ways. In one embodiment, the excitation light source 253 is coupled to the same fiber 306 used to carry captured fluorescence with coupling optics 316. This embodiment may use, for example, a dichromatic filter 314 to direct excitation light through coupling optics 316 and into the optical fiber 306 on substantially the same path as the fluorescence, but in the opposite direction.

Figure 4:
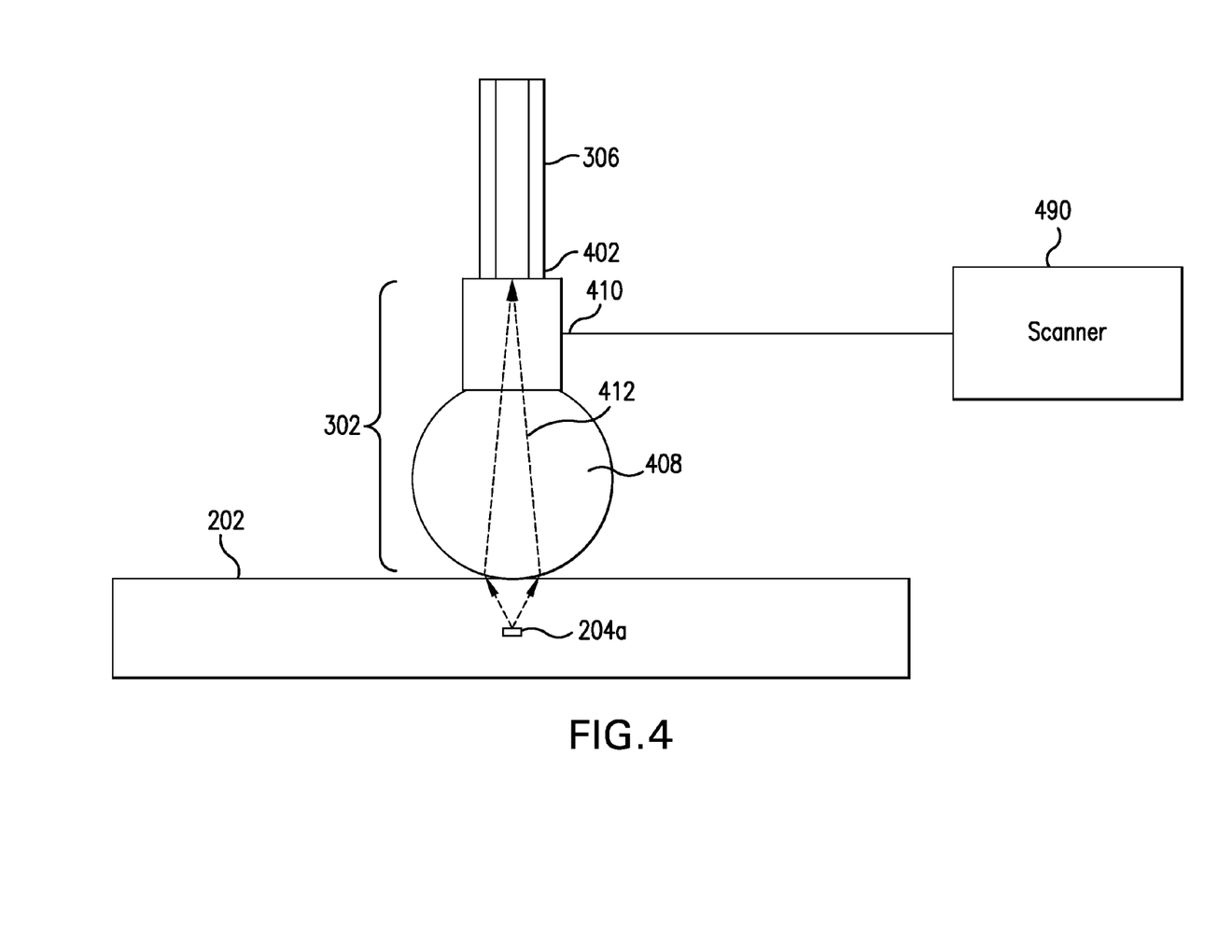
FIG. 4 illustrates an embodiment of the present invention wherein excitation light and fluorescence both travel along the same optical fiber.
Figure 9:
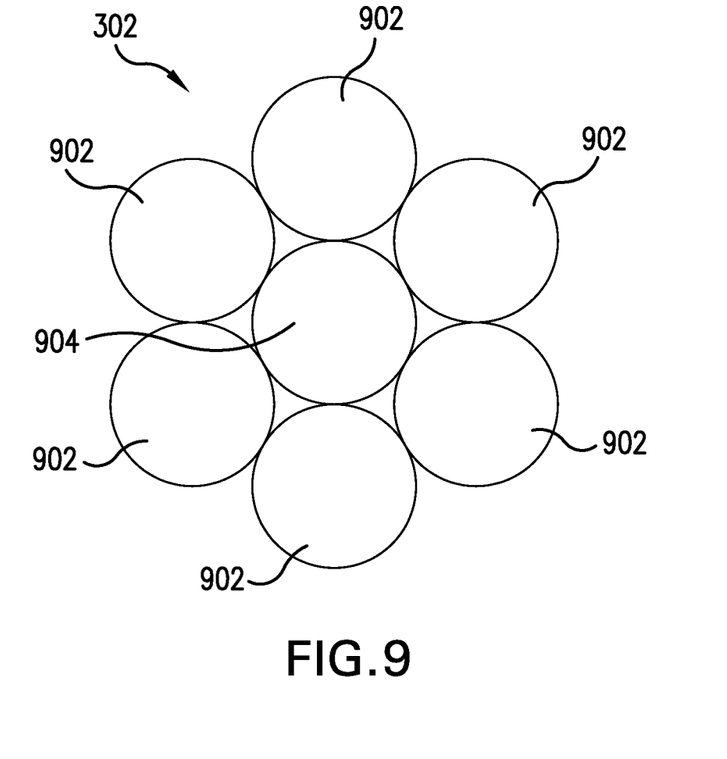
FIG. 9 depicts a bundle of optical fibers.
Figure 10:
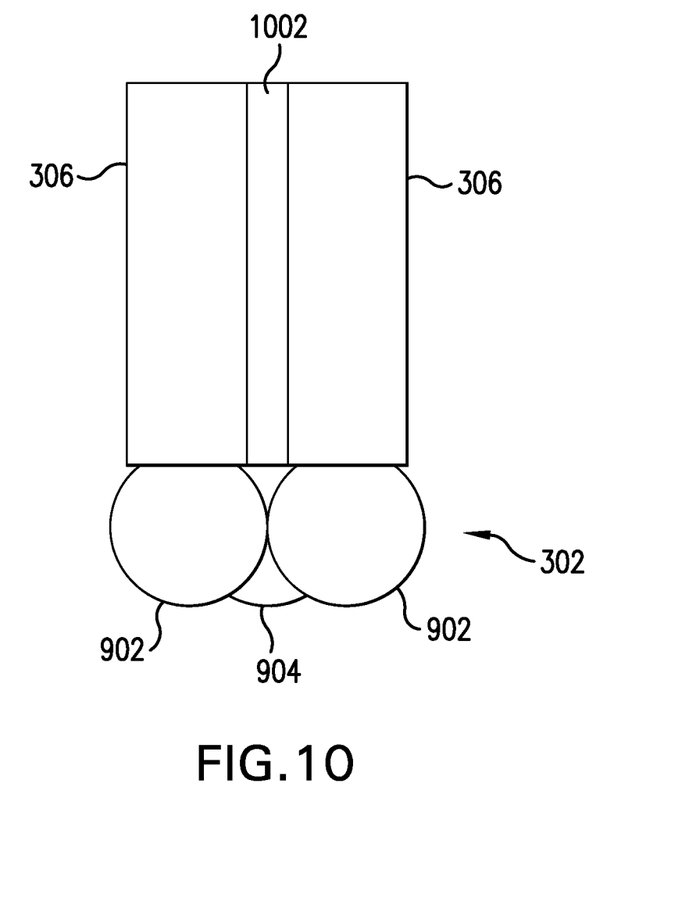
FIG. 10 depicts a positioning system coupled to a probe.

Referring now to FIG. 4, a diagram of a close-up side view of one possible probe head 302 is shown. In general, when light is emitted from the microfluidic channel 204a of microfluidic chip 202, it follows light path 412 and through probe head 302 is collected into the optical fiber 306. It would be understood by one of ordinary skill in the art that optical fiber 306 may comprise a single optical fiber or, as shown in FIGS. 9 & 10, a bundle of optical fibers.

As shown in FIG. 4, probe head may include a light collecting element 408 connected to the distal end 402 of each optical fiber 306. Light collecting element 408 may comprise one or more of a high-index spherical lens, gradient index lens, a Fresnel lens, a micro-lens system, a lensed fiber, or any combination thereof. Probe head 302 may further comprise a spacer 410 positioned between the end 402 of the fiber 306 and light collecting element 408. Preferably, probe head 302 is integrally connected to the optical fiber 306.

Probe head 302 is designed to capture a significant fraction of the light emitted from within a channel of the microfluidic device 202. By positioning the probe head 302 close to the outer surface of the device, it is possible to achieve reasonably high collection efficiency with a relatively small diameter collecting element 408. In one embodiment, desirable collection efficiencies can be achieved by positioning the probe head about 20 millimeters, and preferably about 10 millimeters, from the top of a channel of the microfluidic device 202. Of course, other distances between the probe head and the top of the channel may be used as well.

A scanner 490 can be connected to the probe head to scan the probe head across an area of interest. Scanner 490 may include a positioner (e.g., the MX80 positioner available from Parker Hannifin Corporation of PA ("Parker")) for positioning probe head 302, a stepping drive (e.g., the E-AC Microstepping Drive available from Parker) for driving the positioner, and a controller (e.g., the 6K4 controller available from Parker) for controlling the stepping drive.

Figure 5:
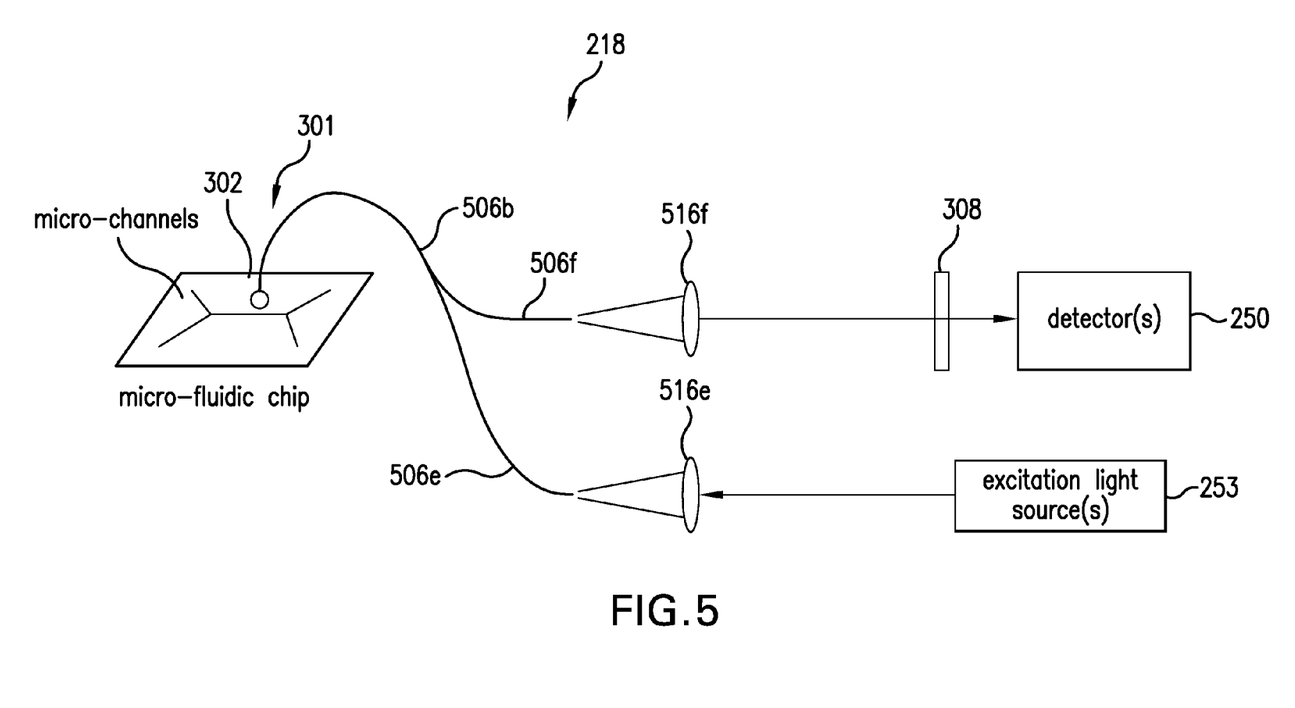
FIG. 5 illustrates an embodiment of the present invention wherein excitation light and fluorescence both travel along the different optical fibers in a bundle of optical fibers.

Referring now to FIG. 5, another embodiment of imaging system 218 is illustrated. In the embodiment shown, the excitation light can be carried by at least one separate optical fiber. As shown in FIG. 5, light from the excitation source or sources 253 is directed through the coupling optics 516e to excitation optical fiber 506e. Similarly, fluorescence from the probe head 302 is directed from fluorescence optical fiber 506f through the coupling optics 516f to filters 308 and the detector or detectors 250. Fluorescence optical fiber 506f and excitation optical fiber 506e can be bundled together to form optical bundle 506b.

Figure 6:
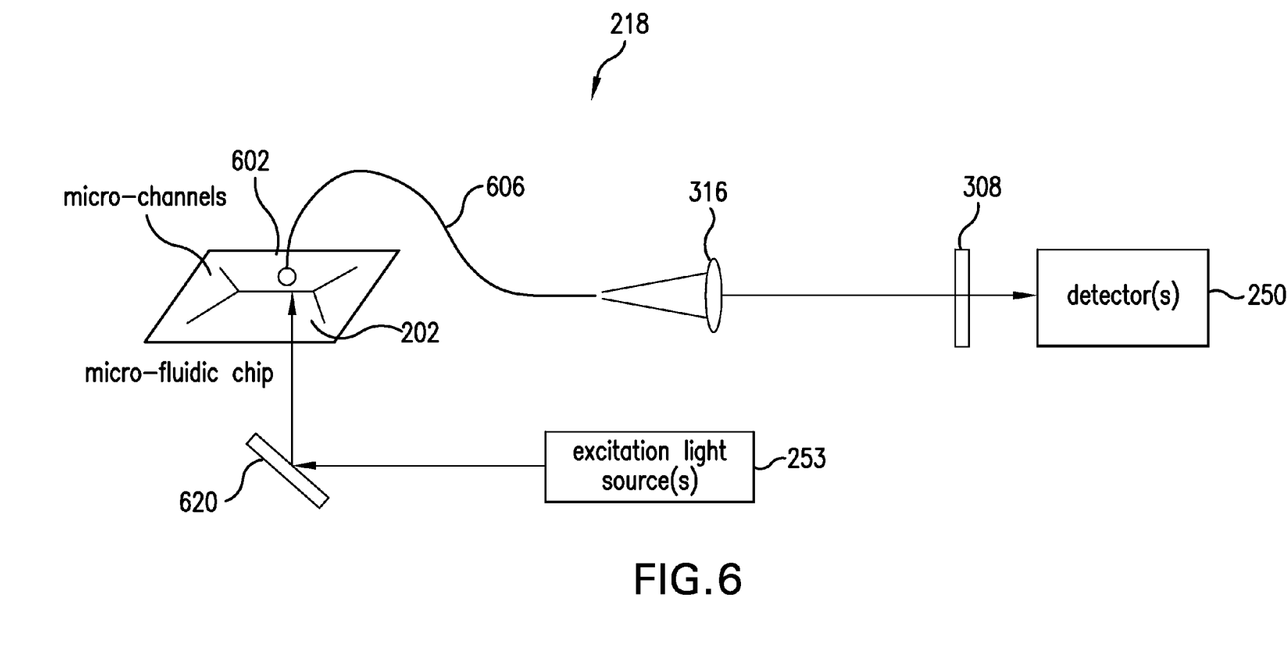
FIG. 6 illustrates an embodiment of the present invention wherein the excitation light is directed on to the sample without going through an optical fiber.

Referring now to FIG. 6, another embodiment of imaging system 218 is illustrated. In the embodiment shown in FIG. 6, the excitation light is not carried by a fiber, but is directed into the micro-channel through free space. As shown in FIG. 6, light from the excitation light source or sources 253 is directed on to the microfluidic chip 202 using mirror 620. Mirror 620 may be movable so as to be capable of directing the excitation light on to any desired point on the microfluidic chip 202.

Figures 7A, 7B:
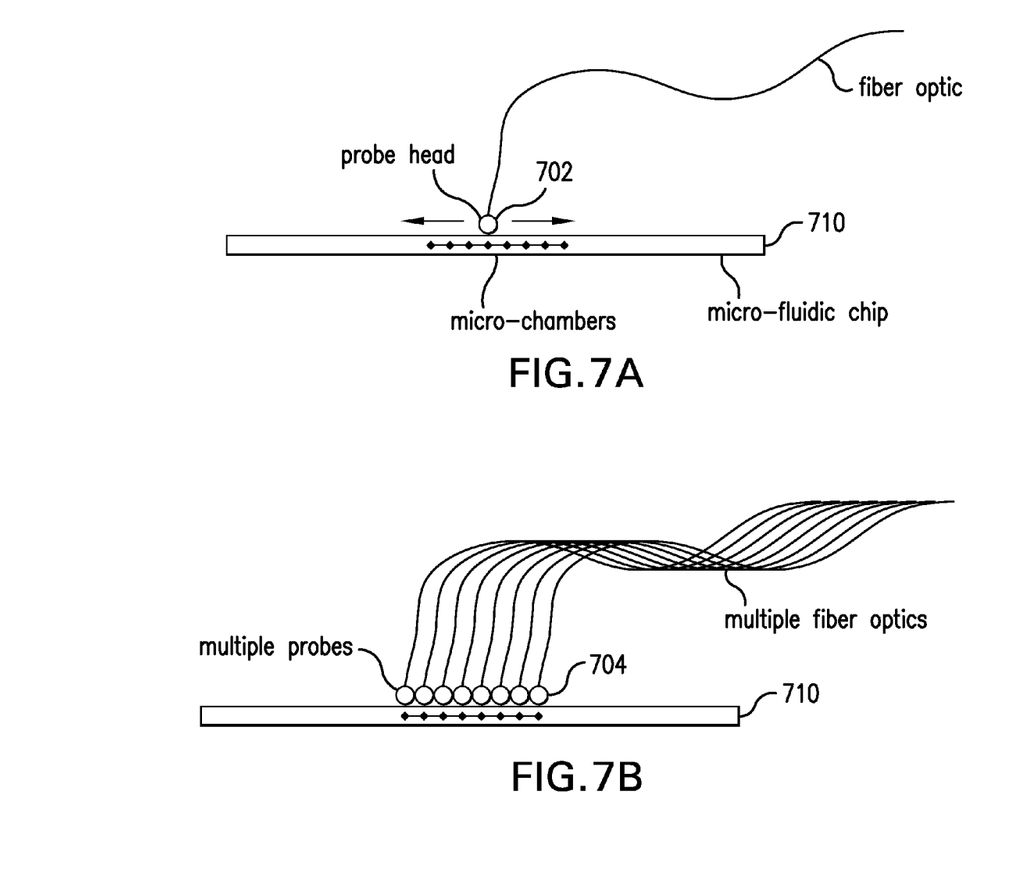
FIG. 7A depicts a cross-sectional view of a version of the present invention utilizing a single probe.
FIG. 7B depicts a cross-sectional view of a version of the present invention utilizing multiple probes.

Referring now to FIGS. 7A and 7B, a comparison of a single fiber optic probe to a multiple fiber optic probe configuration is shown. A single probe 702 may be connected to a scanner that scans the probe over an area of interest from different locations in series. The single probe 702 can be scanned in one or two dimensions across the face of the microfluidic chip 710.

Alternatively, in the embodiment shown in FIG. 7B, a plurality of fiber optic probes 704 may be fixed with respect to the microfludic chip 710, and each collects fluorescence signal data from one location. As an alternative to being fixed, the plurality of probe heads 704 could be configured so that they can be scanned over an area of interest and each probe head 704 can be used to gather image data from a section of the total area of interest.

An advantage of using multiple probes at the same time is that use of multiple probes creates some degree of parallelism and could be used to decrease the time required to collect the desired image data. This is especially true if the probe diameter is comparable to, or smaller than the required spatial resolution in a particular direction.

Figure 8A:
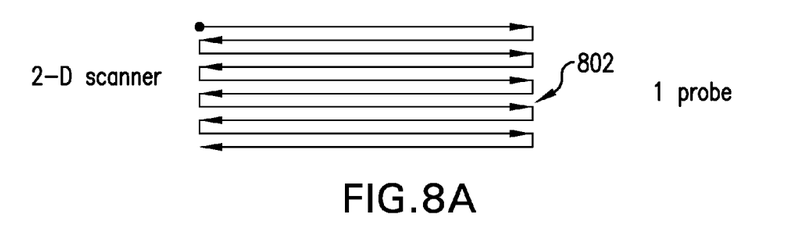
FIGS. 8A-8D illustrate a few of many possible trajectories probes may take to scan an area of interest.
Figure 8B:
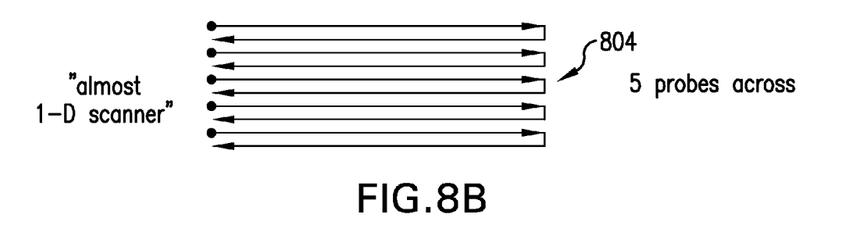
Figure 8C:
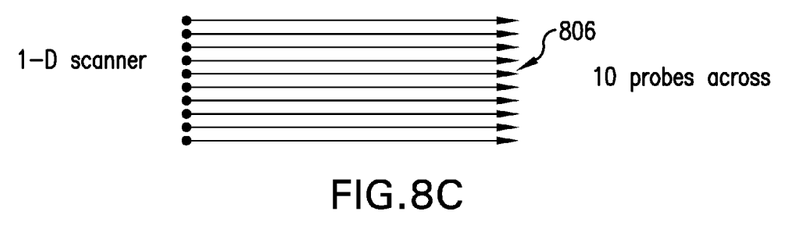
Figure 8D:
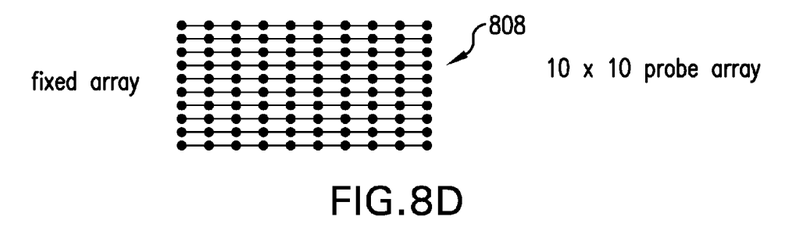

Depending on a combination of parameters (e.g. probe head size, required spatial resolution, required signal acquisition durations, etc.), a number of possible acquisition sequences and scanning trajectories are possible. FIGS. 8A-8D illustrate a few of the possible scanning trajectories. As shown in FIG. 8A, a 2-D scanner trajectory 802 could be used with a single probe. In this trajectory, the probe is moved over an area of interest in two dimensions. As shown in FIG. 8B, by using more probes (e.g. five) an "almost" 1-D scanner trajectory 804 may be adopted wherein several are scanned in one direction and then back again. The trajectory of FIG. 8C uses even more probes. A 1-D scanner trajectory 806 can be used wherein the several probes are only moved across the area of interest in one direction. FIG. 8D shows another trajectory option: a fixed array 808 of probes.

Referring now to FIGS. 9 and 10, another embodiment of probe head 302 is illustrated. Probe head 302 can comprise perimeter probe heads 902 and one or more inner probe heads 904. Each probe head 902 and 904 can be connected to a different optical fiber 306 or 1002 (as shown in FIG. 10). Optical fibers 306 can direct excitation light through perimeter probe heads 902 and optical fiber 1002 can direct fluorescence collected by inner probe head to a light detector. Each perimeter probe head 904 may emit the same frequency of excitation light or different frequencies. It would be understood by those of ordinary skill in the art that different configurations are also possible. For instance, perimeter probe heads could be connected to a detector to detect fluorescence or different detectors and inner probe head could emit excitation light. Alternatively, some combination of inner and perimeter probe heads could emit excitation light and some combination of inner and perimeter probe heads could detect fluorescence.

While various embodiments/variations of the present invention have been described above, it should be understood that they have been presented by way of example only, and not limitation. Thus, the breadth and scope of the present invention should not be limited by any of the above-described exemplary embodiments. Further, unless stated, none of the above embodiments are mutually exclusive. Thus, the present invention may include any combinations and/or integrations of the features of the various embodiments.

Additionally, while the processes described above and illustrated in the drawings are shown as a sequence of steps, this was done solely for the sake of illustration. Accordingly, it is contemplated that some steps may be added, some steps may be omitted, and the order of the steps may be rearranged.

What is claimed is:

1. A method of performing real-time PCR comprising:
   moving a sample of test solution containing real-time PCR reagents through a channel;
   while the sample is moving through a section of the channel:
   cycling the temperature of the sample in order to achieve PCR;
   illuminating the sample with excitation light; and
   using a fiber optic probe to capture fluorescent light emitted from the sample,
   wherein said fiber optic probe includes: (i) an optical fiber having a proximal end and a distal end, and (ii) a probe head connected to and positioned adjacent to the distal end of the optical fiber, said probe head positioned such that at least a portion of the section of the channel is within a field of view of the probe head; and
   measuring the intensity of said fluorescent light.

2. The method of claim 1, wherein said probe head is positioned directly above the channel and is positioned no more than about 10 millimeters from the top of the channel.

3. The method of claim 1, further comprising moving the fiber optic probe along at least the section of the channel while using the fiber optic probe to capture the fluorescent light.

4. The method of claim 3, wherein the speed at which the fiber optic probe is moved along the section of the channel is greater than the speed at which the sample moves through the channel.

5. The method of claim 4, wherein the speed at which the fiber optic probe is moved along the section of the channel is greater than about 10 times the speed at which the sample moves through the channel.

6. The method of claim 1, further comprising using a second fiber optic probe to capture fluorescent light emitted from the sample while the sample is moving through the section of the channel.

7. The method of claim 6, wherein, all the while the sample is moving through the section of the channel, the first fiber optic probe and the second fiber optic probe are fixed in position relative to the channel.

* * * * *